US012812744B2

(12) United States Patent
Thotagamuwa

(10) Patent No.: US 12,812,744 B2
(45) Date of Patent: Nov. 24, 2026

(54) METHOD AND DEVICE FOR CONTROLLING LIGHT OUTPUT BASED ON JUNCTION TEMPERATURE

(71) Applicant: LUMITEX, INC., Strongsville, OH (US)

(72) Inventor: Dinusha Thotagamuwa, Strongsville, OH (US)

(73) Assignee: LUMITEX, INC., Strongsville, OH (US)

( * ) Notice: Subject to any disclaimer, the term of this patent is extended or adjusted under 35 U.S.C. 154(b) by 129 days.

(21) Appl. No.: 18/853,232

(22) PCT Filed: Apr. 26, 2022

(86) PCT No.: PCT/US2022/026328
§ 371 (c)(1),
(2) Date: Oct. 1, 2024

(87) PCT Pub. No.: WO2023/211426
PCT Pub. Date: Nov. 2, 2023

(65) Prior Publication Data
US 2025/0227827 A1 Jul. 10, 2025

(51) Int. Cl.
*H05B 45/14* (2020.01)
*A61N 5/06* (2006.01)
*H05B 45/18* (2020.01)

(52) U.S. Cl.
CPC ........... *H05B 45/18* (2020.01); *A61N 5/0616* (2013.01); *H05B 45/14* (2020.01); *A61N 2005/0627* (2013.01); *A61N 2005/0652* (2013.01)

(58) Field of Classification Search
CPC ........ H05B 45/10; H05B 45/12; H05B 45/14; H05B 45/18; H05B 45/22; H05B 45/28; A61N 5/0616; A61N 5/062; A61N 2005/0627
See application file for complete search history.

(56) References Cited

U.S. PATENT DOCUMENTS

| | | | | |
|---|---|---|---|---|
| 8,193,737 B2 * | 6/2012 | Peker | G09G 3/3413 | 315/297 |
| 2007/0040512 A1 * | 2/2007 | Jungwirth | H05B 45/22 | 315/159 |
| 2008/0007182 A1 * | 1/2008 | Deurenberg | H05B 45/28 | 315/149 |

(Continued)

FOREIGN PATENT DOCUMENTS

| | | |
|---|---|---|
| WO | 2010103413 A1 | 9/2010 |
| WO | 2011024098 A1 | 3/2011 |

OTHER PUBLICATIONS

International Search Report and Written Opinion (ISRWO) corresponding to counterpart International Patent Application PCT/US2022/026328 mailed Feb. 12, 2022.

*Primary Examiner* — Thai Pham
(74) *Attorney, Agent, or Firm* — Renner, Otto, Boisselle & Sklar, LLP

(57) ABSTRACT

The present disclosure provides a method and control circuitry for controlling light output from a light emitting diode (LED). Light output is controlled based on a measured temperature of a junction of the LED. An electrical current is supplied to the LED based on the measured temperature, such that the light emitting diode outputs a desired optical output.

20 Claims, 3 Drawing Sheets

(56) References Cited

U.S. PATENT DOCUMENTS

| | | | | |
|---|---|---|---|---|
| 2008/0215279 | A1* | 9/2008 | Salsbury | H05B 45/28 702/107 |
| 2009/0189530 | A1* | 7/2009 | Ashdown | H05B 45/22 315/152 |
| 2011/0241572 | A1* | 10/2011 | Zhang | H05B 45/18 315/308 |
| 2012/0146548 | A1* | 6/2012 | Campbell | H05B 45/18 315/297 |
| 2013/0296978 | A1 | 11/2013 | Fiset | |

* cited by examiner

METHOD AND DEVICE FOR CONTROLLING LIGHT OUTPUT BASED ON JUNCTION TEMPERATURE

This application is a national phase of International Application No. PCT/US2022/026328 filed Apr. 26, 2022, which is incorporated herein by reference in its entirety.

TECHNICAL FIELD

The present disclosure relates generally to phototherapy devices and more particularly to a method and device for controlling light emission from a light emitting diode.

BACKGROUND

Phototherapy is increasingly being used to treat various maladies such as jaundice in infants. During phototherapy treatment, it is important to ensure that the optical dosage applied to a patient is sufficiently strong to achieve the desired physiological effect without being strong enough to cause harm (e.g., burns).

SUMMARY

Phototherapy devices typically rely on predetermined settings to control optical dosage, but simply relying on predetermined settings as an estimate for optical dosage does not account for changes in the light source that result in variations in optical dosage for specified parameters (e.g., caused by aging of the components, increase, or decrease in temperature, etc.).

The present disclosure provides a method and device for controlling light output from a light emitting diode (LED) using current and a calibration setting that varies based on a junction temperature. In one embodiment, sensor measurements are used as a control feedback signal to modulate the current supplied to the light emitting diode to maintain consistent optical output of the light emitting diode.

The optical output of a light emitting diode is proportional to a forward current when a junction temperature of the light emitting diode is held constant. To compensate for the junction temperature deviating from a calibrated temperature (e.g., a standard operating temperature), a calibration factor may be applied to the electrical current supplied to the light emitting diode to maintain a consistent output of the light emitting diode. For example, the forward voltage (Vf) of the light emitting diode may be measured and used to determine the junction temperature of the light emitting diode and a correction factor corresponding to the determined junction temperature may be applied to the electrical current supplied to the light emitting diode.

While a number of features are described herein with respect to embodiments of the invention; features described with respect to a given embodiment also may be employed in connection with other embodiments. The following description and the annexed drawings set forth certain illustrative embodiments of the invention. These embodiments are indicative, however, of but a few of the various ways in which the principles of the invention may be employed. Other objects, advantages, and novel features according to aspects of the invention will become apparent from the following detailed description when considered in conjunction with the drawings.

BRIEF DESCRIPTION OF THE DRAWINGS

The annexed drawings, which are not necessarily to scale, show various aspects of the invention in which similar reference numerals are used to indicate the same or similar parts in the various views.

DETAILED DESCRIPTION

The present disclosure provides a method and control circuitry for controlling light output from a light emitting diode (LED). Light output is controlled based on a measured temperature of a junction of the light emitting diode. An electrical current is supplied to the light emitting diode based on the measured temperature, such that the light emitting diode outputs a desired optical output (e.g., a predetermined radiant flux). As used herein, desired optical output may describe a predetermined radiant flux, optical intensity, optical dosage, or any other suitable measure of light output.

Figure 1:
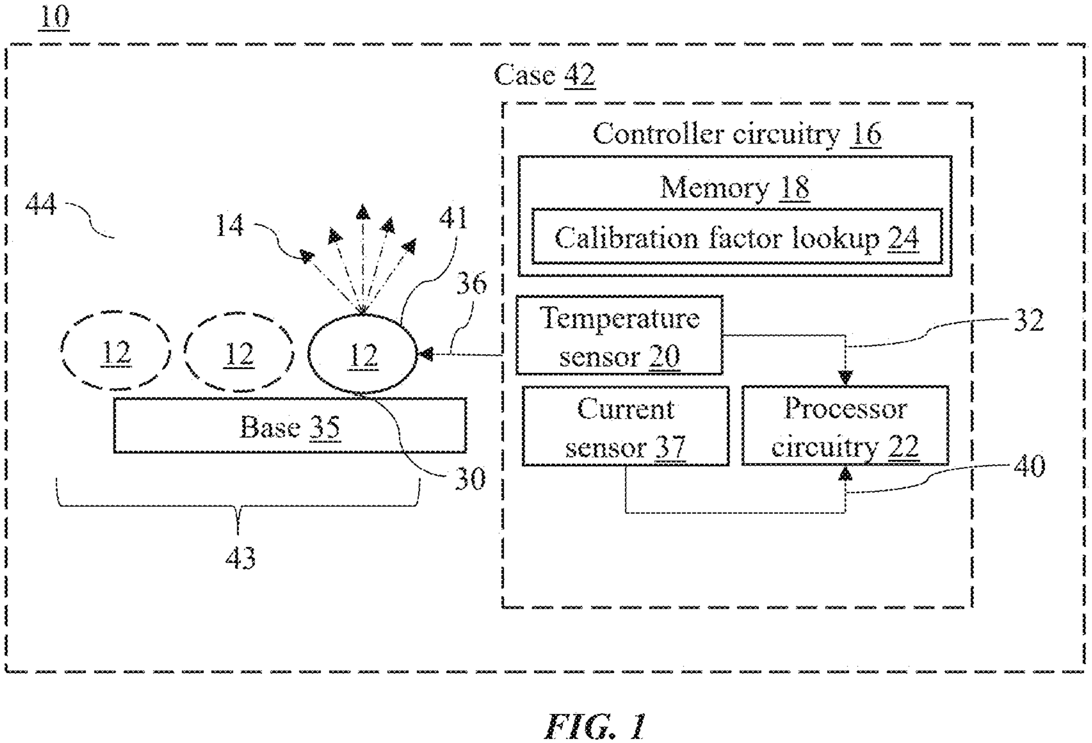
FIG. 1 is a schematic diagram of an exemplary embodiment of a light source having a feedback loop for maintaining optical output at a desired output.
Figure 2:
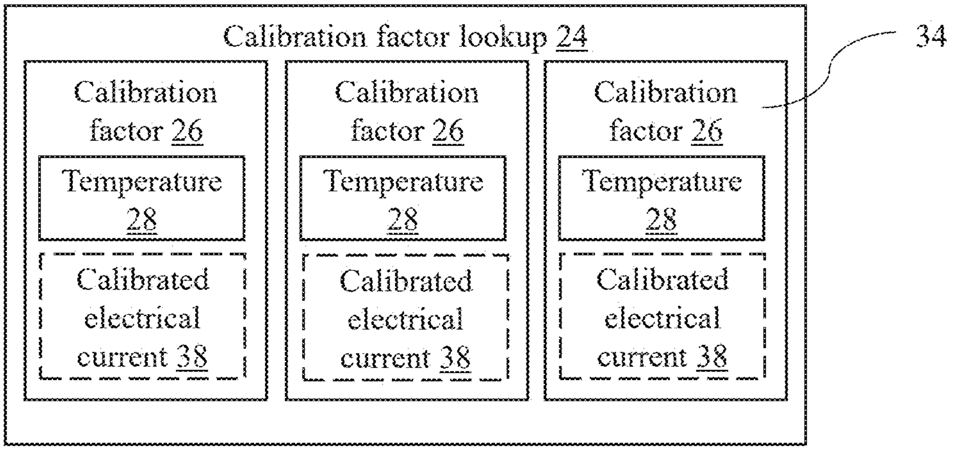
FIG. 2 is a schematic diagram of an exemplary embodiment of a calibration factor lookup.

Turning to FIGS. 1 and 2, an exemplary embodiment is shown of a light source 10 having a feedback loop for maintaining optical output at a desired output. The light source 10 includes a light emitting diode 12 that emits light 14, controller circuitry 16 for modulating the emission of light 14 from the light emitting diode 12. The controller circuitry 16 includes memory 18, a temperature sensor 20, and processor circuitry 22. The memory 18 stores a calibration factor lookup 24 that includes multiple calibration factors 26. As shown in FIG. 2, each of the multiple calibration factors 26 is associated with a temperature 28 for a desired optical output by the light emitting diode 12. The temperature sensor 20 measures a temperature 32 of a junction 30 of the light emitting diode 12. The processor circuitry 22 receives the measured temperature 32 from the temperature sensor 20 and identifies one of the multiple calibration factors 26 from the calibration factor lookup 24 as a selected calibration factor 34 based on the received measured temperature 32. The processor circuitry 22 controls an electrical current 36 supplied to the light emitting diode 12 based on the selected calibration factor 34, such that the light emitting diode 12 outputs the desired optical output.

Figure 3:
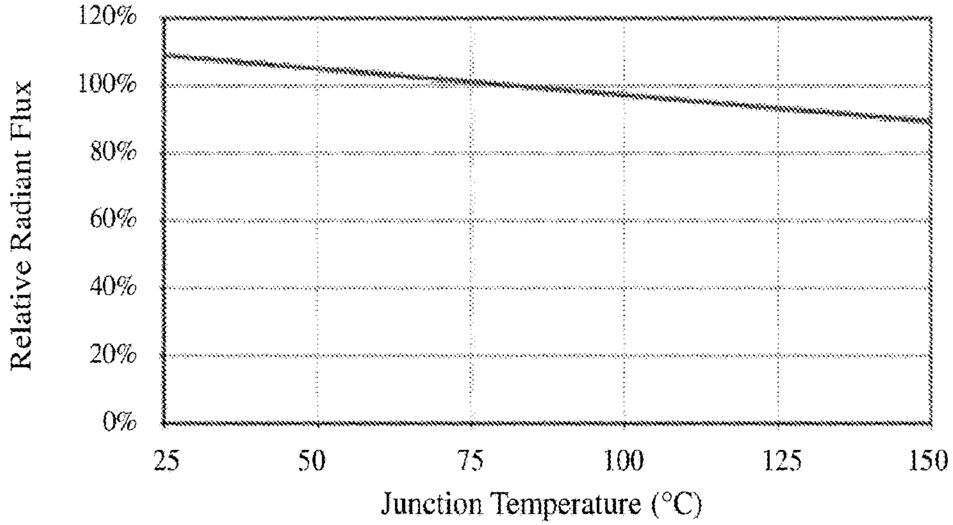
FIG. 3 is an exemplary plot depicting the relationship between junction temperature and relative radiant flux for a light source.

An exemplary relationship between junction temperature and optical output (radiant flux in this example) is shown in FIG. 3. As shown, a low junction temperature typically increases photon production and reduces lumen depreciation, increasing radiant flux. The calibration factors 26 stored in the calibration factor lookup 24 and the temperature 28 associated with each of the calibration factors 26 may be determined based on the relationship shown in FIG. 3.

In one embodiment, the controller circuitry 16 also includes a current sensor 37 for measuring an electrical current 36 supplied to the light emitting diode 12. The processor circuitry 22 may identify a calibrated electrical current 38 based on the selected calibration factor 34. For example, the selected calibration factor 34 may directly specify the calibrated electrical current 38 as shown in FIG. 2. that is, the calibration factors 26 in the lookup table 24 may specify a specific current value. As another example, the processor circuitry 22 may supply a default current to the light emitting diode 12 unless altered by a calibration factor 34. In this example, the processor circuitry 22 may control the electrical current 36 supplied to the light emitting diode 12 based on a product of the selected calibration factor 34 and the default current.

The processor circuitry 22 may repeatedly receive a measured electrical current 40 from the current sensor and cyclically control the electrical current 36 supplied to the light emitting diode 12 based on the identified calibrated electrical current 38 and the received measured electrical current 40, such that the measured electrical current 40 matches the calibrated electrical current 38. That is, the processor circuitry 22 may act as a feedback loop to ensure that the calibrated electrical current 38 is supplied to the light emitting diode 12. The measured electrical current may be considered to match the calibrated electrical current when the measured electrical current differs from the calibrated electrical current by less than ten percent, less than twenty percent, or less than thirty percent.

In one embodiment, the processor circuitry 22 repeatedly receives a currently measured temperature 32 from the temperature sensor 20. The processor circuitry 22 may use this received currently measured temperature 32 to identify as the selected calibration factor 34 (also referred to as the currently selected calibration factor) the calibration factor 26 from the calibration factor lookup 24 that corresponds to the currently measured temperature 32. That is, the processor circuitry 22 may determine the currently selected calibration factor 34 from the calibration factor lookup 24 based on the currently measured temperature 32. For example, the calibration factor lookup 24 may be a lookup table listing a temperature (or temperature range) in association with a calibration factor 26. The processor circuitry 22 may then select as the currently selected calibration factor 34 the calibration factor 26 associated with the currently measured temperature 32. The processor circuitry 22 may identify a new selected calibration factor 34 (i.e., the current selected calibration factor) when a measured temperature 32 is received.

In this embodiment, the processor circuitry 22 may also cyclically control the electrical current 36 supplied to the light emitting diode 12 based on the currently selected calibration factor 34, such that the output of the light emitting diode 12 is maintained at the desired optical output. For example, the processor circuitry 22 may maintain the light emission by the light emitting diode 12 within a predetermined range of radiant flux by altering the electrical current 36 supplied to the light emitting diode 12 based on the measured temperature 32.

The temperature sensor 20 may be any suitable device for determining temperature at the junction 30 of the light emitting diode 12, such as a thermocouple or thermistor. The junction temperature may be defined as the temperature of an active region of the light emitting diode (i.e., the location where the diode connects to the base 35). The junction 30 may be defined as the location where electrons jump between two semiconductors to produce photons.

Figure 5:
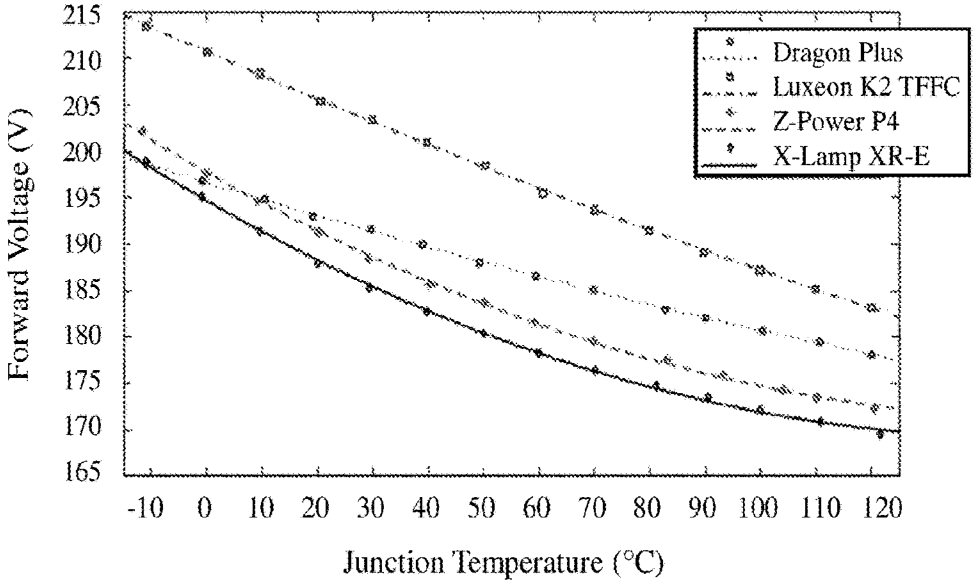
FIG. 5 is an exemplary plot depicting the relationship between junction temperature and forward voltage for four different light sources.

In one embodiment, the temperature sensor 20 may be a voltage sensor that measures a forward voltage of the light emitting diode 12. The processor circuitry 22 may receive the measured forward voltage of the light emitting diode 12 and convert the forward voltage measurement to a junction temperature using a lookup table and/or a known relationship between forward voltage and junction temperature. For example, the lookup table may be a plot or list of values as shown in FIG. 5. FIG. 5 shows a relationship between junction temperature and forward voltage for four different light sources. The memory 18 may store this information for the light emitting diode 12 and the processor circuitry 22 may use this information to determine the junction temperature of the light emitting diode based on the measured forward voltage.

Figure 4:
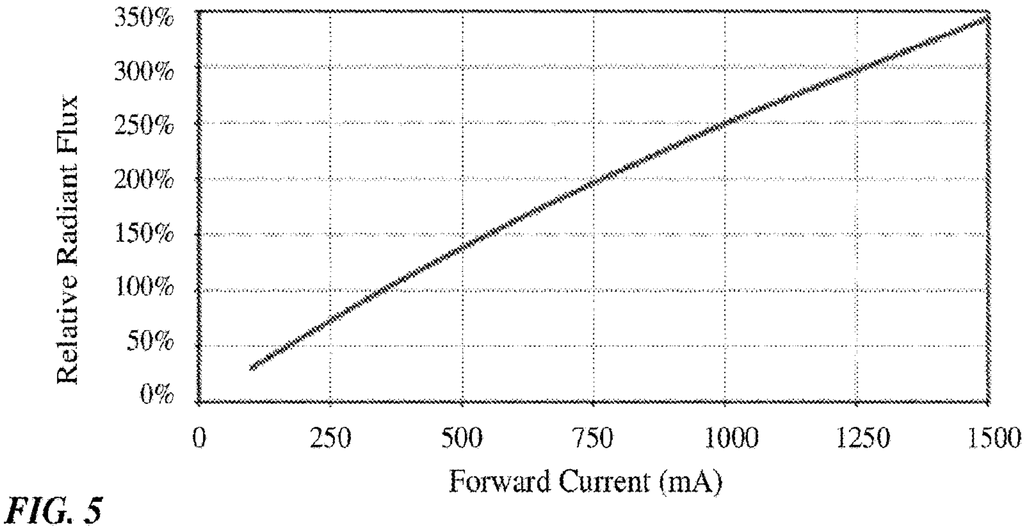
FIG. 4 is an exemplary plot depicting the relationship between electrical current temperature and relative radiant flux for a light source.

In one embodiment, the controller circuitry 16 includes a current sensor 37 for measuring an electrical current 36 supplied to the light emitting diode 12. The processor circuitry 22 may repeatedly receive a measured electrical current 40 from the current sensor 37 as a presently measured electrical current. The processor circuitry 22 may cyclically determine a current optical output of the light emitting diode 12 based on the presently measured electrical current 40 (i.e., the measurement received from the current sensor 37). For example, FIG. 4 depicts a relationship between forward current and optical output (radiant flux in this example). The processor circuitry 22 may use a lookup table or known relationship (such as a graph similar to FIG. 4) to determine the optical output of the light emitting diode 12 based on the measured electrical current 40.

In this embodiment, as described above, the processor circuitry 22 may also identify the calibrated electrical current based on the selected calibration factor (e.g., which was selected based on the measured temperature 32). The processor circuitry 22 may cyclically control the electrical current 36 supplied to the light emitting diode 12 based on the calibrated electrical current and the presently measured electrical current, such that the presently measured electrical current matches the calibrated electrical current. For example, the measured electrical current may match the calibrated electrical current if the measured electrical current differs from the calibrated electrical current by less than ten percent, less than twenty percent, or less than thirty percent.

Measurements from the sensor may be received by the processor circuitry 22 at any suitable frequency. Similarly, the processor circuitry 22 may determine a calibration factor and/or calibrated electrical current at any suitable frequency and/or based on when sensor measurements are received.

As shown in FIG. 1, the light emitting diode 12 may be a representative light emitting diode 41 of a plurality of light emitting diodes 43. The controller circuitry 16 may supply the same electrical current 36 to the plurality of light emitting diodes 43 as the representative light emitting diode 41. That is, the electrical current 36 supplied to the plurality of light emitting diodes 43 may be based on the selected calibration factor identified from the measured temperature of the junction 30 of the representative light emitting diode 41. In this embodiment, the measurements of properties of a representative light emitting diode 41 are used to control the electrical current supplied to a plurality of light emitting diodes 43 (e.g., an array of light emitting diodes).

In one embodiment, the light emitting diode 12 may be housed within an interior 44 of a case 42 and the temperature sensor 20 may be positioned to measure the temperature 28 of the junction 30 of the light emitting diode 12 by measuring the temperature 28 of the interior 44 of the case 42.

In one embodiment, the processor circuitry 22 may stop light emission by the light emitting diode 12 (e.g., by reducing the supply of electrical power to the light emitting diode 12) when the measured temperature 32 is outside of a defined acceptable temperature range. For example, a wavelength of the light output by the light emitting diode 12 may be dependent upon the junction temperature of the light emitting diode 12. For this reason, if the measured temperature is outside of an acceptable range (e.g., a temperature range where the wavelength range of the light output by the light emitting diode 12 falls within a desired wavelength), then the processor circuitry 22 may stop light output by the light emitting diode 12 when the measured temperature is not within the acceptable range (i.e., a predetermined temperature range).

In one embodiment, the processor circuitry 22 is electrically connected to the light emitting diode 12 and is configured to control properties of light emitted by the light emitting diode 12 such as intensity. That is, the processor circuitry 22 may modulate the amount of light delivered by the light emitting diode 12. The processor circuitry 22 may modulate the amount of light to provide a therapeutically effective dose (e.g., to treat jaundice in an infant).

The processor circuitry 22 may have various implementations. For example, the processor circuitry 22 may include any suitable device, such as a processor (e.g., CPU), programmable circuit, integrated circuit, memory and I/O circuits, an application specific integrated circuit, microcontroller, complex programmable logic device, other programmable circuits, or the like. The processor circuitry 22 may also include a non-transitory computer readable medium, such as random-access memory (RAM), a read-only memory (ROM), an erasable programmable read-only memory (EPROM or Flash memory), or any other suitable medium.

The memory 18 may be any suitable computer readable medium, such as a non-transitory computer readable medium. For example, the memory 18 may be one or more of a buffer, a flash memory, a hard drive, a removable media, a volatile memory, a non-volatile memory, a random-access memory (RAM), or other suitable device. In a typical arrangement, the memory 18 may include a non-volatile memory for long term data storage and a volatile memory that functions as system memory for the processor circuitry 22. The memory 18 may exchange data with the circuitry over a data bus. Accompanying control lines and an address bus between the memory 18 and the circuitry also may be present. The computer readable medium 18 is considered a non-transitory computer readable medium.

The light source 10 may additionally include a power source that provides electrical power to at least one of the processor circuitry 22 or the light emitting diode 12. The power source may be any suitable source of electrical power, such as a battery or a plug configured to receive electrical power from an external power source. Unless specifically stated otherwise, references to "a," "an," and/or "the" may include one or more than one, and that reference to an item in the singular may also include the item in the plural.

Figure 6:
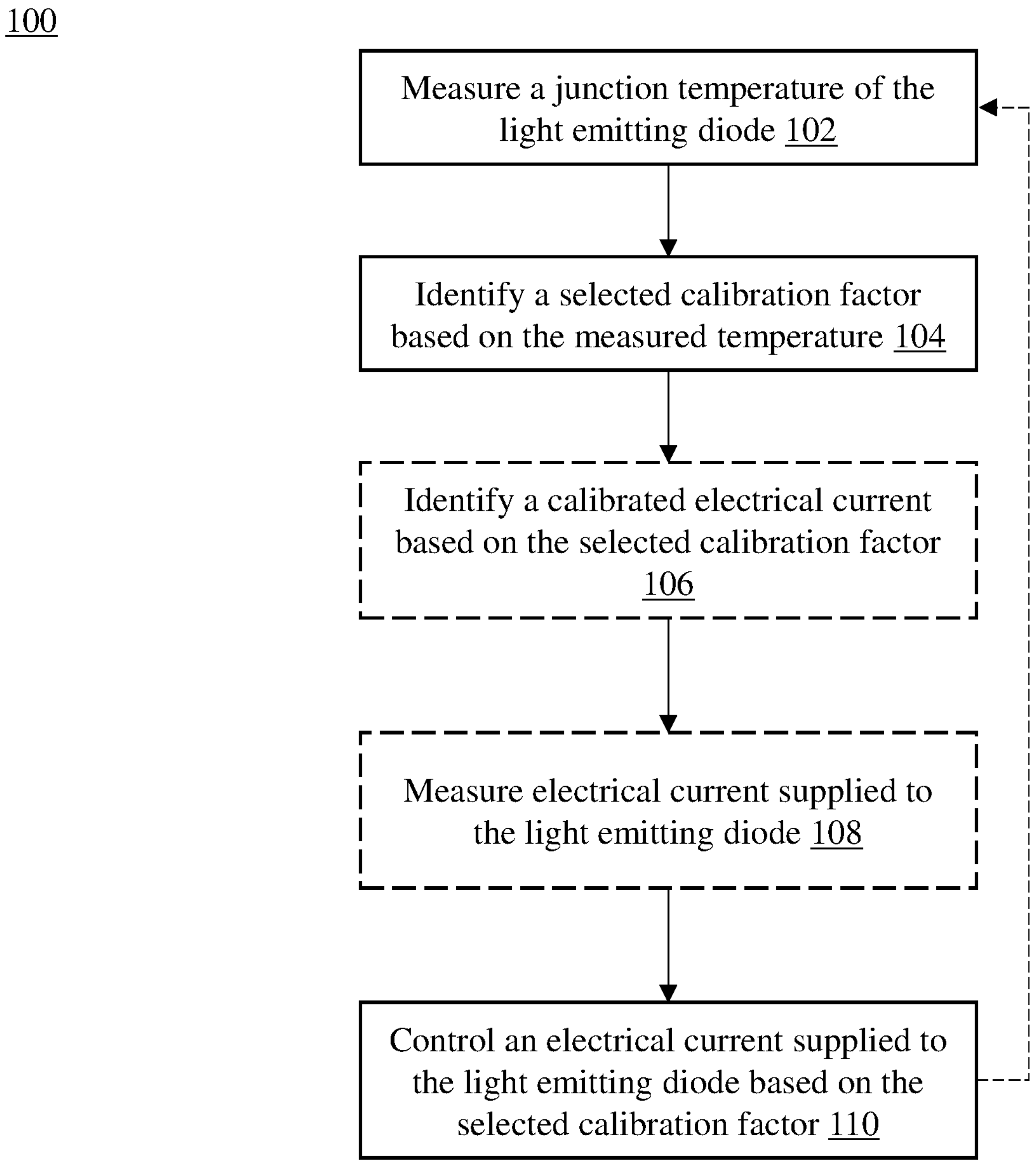
FIG. 6 is a flow chart of an exemplary method for controlling light emission from a light emitting diode.

In the exemplary embodiment depicted in FIG. 6, a method 100 is shown for controlling light emission from the light emitting diode 12 using controller circuitry 16. In step 102, a temperature 28 is measured of a junction 30 of the light emitting diode 12 using a temperature sensor 20 of the controller circuitry 16. In step 104, the processor circuitry 22 identifies a selected calibration factor 34 from a calibration factor lookup 24 based on the measured temperature 32.

In optional step 106, a calibrated electrical current is identified based on the selected calibration factor. For example, the selected calibration factor may specify the calibrated electrical current or the calibrated electrical current may be determined based on the selected calibration factor (e.g., multiplying the selected calibration factor by a default current).

In optional step 108, the electrical current supplied to the light emitting diode is measured using the current sensor of the controller circuitry 16. For example, the electrical current supplied 36 to the light emitting diode 12 may not be directly measured, but the forward current of the light emitting diode 12 may instead be measured.

In step 110, the processor circuitry 22 controls an electrical current 36 supplied to the light emitting diode 12 based on the selected calibration factor, such that the light emitting diode 12 outputs the desired optical output. For example, the electrical current supplied to the light emitting diode 12 may be controlled using the processor circuitry 22 based on the identified calibrated electrical current and the received measured electrical current, such that the measured electrical current matches the calibrated electrical current.

In one embodiment, after measuring the electrical current supplied to the light emitting diode in step 108, step 110 includes determining using the processor circuitry 22 a current optical output of the light emitting diode based on the presently measured electrical current (e.g., based on a predetermined relationship between junction temperature, forward current, and optical output as shown in FIGS. 3-5). In this embodiment, controlling the current supplied to the light emitting diode based on the selected calibration factor in step 110 includes using the processor circuitry to control the electrical current supplied to the light emitting diode based on the calibrated electrical current and the presently measured electrical current, such that the presently measured electrical current matches the calibrated electrical current. As described above, measured electrical current may be considered to match the calibrated electrical current when the measured electrical current differs from the calibrated electrical current by less than ten percent, less than twenty percent, or less than thirty percent.

Following step 108, processing may optionally return to step 102, e.g., such that a calibrated electrical current is again selected and supplied to the light emitting diode 12. In this way, the currently measured temperature may be repeatedly measured using the temperature sensor and the currently selected calibration factor may be repeatedly identified with the processor circuitry 22 based on the currently measured temperature. Similarly, the electrical current 36 supplied to the light emitting diode 12 may be cyclically controlled using the processor circuitry 22 based on the currently selected calibration factor, such that the output of the light emitting diode 12 is maintained at the desired optical output.

Although the invention has been shown and described with respect to a certain embodiment or embodiments, equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

The invention claimed is:

1. Controller circuitry for modulating light emission from a light emitting diode, the controller circuitry comprising:

memory comprising a non-transitory computer readable medium and storing a calibration factor lookup, wherein:

the calibration factor lookup includes multiple calibration factors and each of the multiple calibration factors is associated with a temperature for a desired optical output by the light emitting diode; and the desired optical output comprises an optical intensity of the light emitting diode;

a temperature sensor configured to measure a temperature of a junction of the light emitting diode; and processor circuitry configured to:

receive the measured temperature from the temperature sensor;

identify one of the multiple calibration factors from the calibration factor lookup as a selected calibration factor based on the received measured temperature; and control an electrical current supplied to the light emitting diode based on the selected calibration factor, such that the light emitting diode outputs the desired optical output.

2. The controller circuitry of claim 1, further comprising a current sensor configured to measure an electrical current supplied to the light emitting diode, wherein the processor circuitry is further configured to:

identify a calibrated electrical current based on the selected calibration factor;

repeatedly receive a measured electrical current from the current sensor; and cyclically control the electrical current supplied to the light emitting diode based on the identified calibrated electrical current and the received measured electrical current, such that the measured electrical current matches the calibrated electrical current.

3. The controller circuitry of claim 2, wherein the measured electrical current matches the calibrated electrical current when the measured electrical current differs from the calibrated electrical current by less than ten percent.

4. The controller circuitry of claim 1, wherein the processor circuitry is configured to:

repeatedly receive as a currently measured temperature the measured temperature from the temperature sensor;

repeatedly identify one of the multiple calibration factors from the calibration factor lookup as a currently selected calibration factor based on the currently measured temperature; and cyclically control the electrical current supplied to the light emitting diode based on the currently selected calibration factor, such that the output of the light emitting diode is maintained at the desired optical output.

5. The controller circuitry of claim 1, wherein the temperature sensor comprises a voltage sensor configured to measure a forward voltage of the light emitting diode and to determine the temperature of the junction of the light emitting diode based on the measured forward voltage of the light emitting diode.

6. The controller circuitry of claim 1, further comprising a current sensor configured to measure an electrical current supplied to the light emitting diode, wherein the processor circuitry is further configured to:

repeatedly receive a measured electrical current from the current sensor as a presently measured electrical current;

cyclically determine a current optical output of the light emitting diode based on the presently measured electrical current;

identify a calibrated electrical current based on the selected calibration factor; and cyclically control the electrical current supplied to the light emitting diode based on the calibrated electrical current and the presently measured electrical current, such that the presently measured electrical current matches the calibrated electrical current.

7. The controller circuitry of claim 1, wherein the light emitting diode is housed in an interior of a case and the temperature sensor is configured to measure the temperature of the junction of the light emitting diode by measuring a temperature of the interior of the case.

8. The controller circuitry of claim 1, wherein the processor circuitry is further configured to stop light emission by the light emitting diode when the measured temperature is outside of a defined acceptable temperature range.

9. The controller circuitry of claim 1, wherein:

the light emitting diode comprises a representative light emitting diode of a plurality of light emitting diodes; and the processor circuitry is further configured to supply the electrical current to the plurality of light emitting diodes based on the selected calibration factor identified from the measured temperature of the junction of the representative light emitting diode.

10. A method for controlling light emission from a light emitting diode using controller circuitry, the method comprising:

measuring a temperature of a junction of the light emitting diode using a temperature sensor of the controller circuitry;

using processor circuitry of the controller circuitry to identify a selected calibration factor from a calibration factor lookup based on the measured temperature, wherein:

the calibration factor lookup is stored in a memory of the controller circuitry;

the calibration factor lookup includes multiple calibration factors; and each of the multiple calibration factors is associated with a temperature for a desired optical output by the light emitting diode;

the desired optical output comprises an optical intensity of the light emitting diode; and controlling using the processor circuitry an electrical current supplied to the light emitting diode based on the selected calibration factor, such that the light emitting diode outputs the desired optical output.

11. The method of claim 10, further comprising:

identifying a calibrated electrical current based on the selected calibration factor;

repeatedly measuring an electrical current supplied to the light emitting diode using a current sensor of the controller circuitry; and cyclically controlling the electrical current supplied to the light emitting diode using the processor circuitry based on the identified calibrated electrical current and the received measured electrical current, such that the measured electrical current matches the calibrated electrical current.

12. The method of claim 10, further comprising:

repeatedly measuring a currently measured temperature using the temperature sensor;

repeatedly identifying with the processor circuitry a currently selected calibration factor based on the currently measured temperature; and cyclically controlling the electrical current supplied to the light emitting diode using the processor circuitry based on the currently selected calibration factor, such that the output of the light emitting diode is maintained at the desired optical output.

13. The method of claim 10, further comprising:

repeatedly measuring as a presently measured electrical current an electrical current supplied to the light emitting diode using a current sensor of the controller circuitry;

cyclically determining using the processor circuitry a current optical output of the light emitting diode based on the presently measured electrical current; and identifying a calibrated electrical current based on the selected calibration factor;

cyclically controlling using the processor circuitry the electrical current supplied to the light emitting diode based on the calibrated electrical current and the presently measured electrical current, such that the presently measured electrical current matches the calibrated electrical current.

14. The method of claim 10:

wherein the light emitting diode comprises a representative light emitting diode of a plurality of light emitting diodes;

further comprising controlling using the processor circuitry an electrical current supplied to the plurality of light emitting diodes based on the selected calibration factor identified from the measured temperature of the junction of the representative light emitting diode.

15. A light source having a feedback loop for maintaining optical output at a desired output, the light source comprising:

a light emitting diode configured to emitted light; and controller circuitry for modulating the emission of light from the light emitting diode, wherein the controller circuitry includes:

memory comprising a non-transitory computer readable medium and storing a calibration factor lookup, wherein:

the calibration factor lookup includes multiple calibration factors and each of the multiple calibration factors is associated with a temperature for a desired optical output by the light emitting diode; and the desired optical output comprises an optical intensity of the light emitting diode;

a temperature sensor configured to measure a temperature of a junction of the light emitting diode; and processor circuitry configured to:

receive the measured temperature from the temperature sensor;

identify one of the multiple calibration factors from the calibration factor lookup as a selected calibration factor based on the received measured temperature; and control an electrical current supplied to the light emitting diode based on the selected calibration factor, such that the light emitting diode outputs the desired optical output.

16. The light source of claim 15, further comprising a current sensor configured to measure an electrical current supplied to the light emitting diode, wherein the processor circuitry is further configured to:

identify a calibrated electrical current based on the selected calibration factor;

repeatedly receive a measured electrical current from the current sensor; and cyclically control the electrical current supplied to the light emitting diode based on the identified calibrated electrical current and the received measured electrical current, such that the measured electrical current matches the calibrated electrical current.

17. The light source of claim 15, wherein the processor circuitry is configured to:

repeatedly receive as a currently measured temperature the measured temperature from the temperature sensor;

repeatedly identify one of the multiple calibration factors from the calibration factor lookup as a currently selected calibration factor based on the currently measured temperature; and cyclically control the electrical current supplied to the light emitting diode based on the currently selected calibration factor, such that the output of the light emitting diode is maintained at the desired optical output.

18. The light source of claim 15, further comprising a current sensor configured to measure an electrical current supplied to the light emitting diode, wherein the processor circuitry is further configured to:

repeatedly receive a measured electrical current from the current sensor as a presently measured electrical current;

cyclically determine a current optical output of the light emitting diode based on the presently measured electrical current;

identify a calibrated electrical current based on the selected calibration factor; and cyclically control the electrical current supplied to the light emitting diode based on the calibrated electrical current and the presently measured electrical current, such that the presently measured electrical current matches the calibrated electrical current.

19. The light source of claim 15, wherein the light emitting diode is housed in an interior of a case and the temperature sensor is configured to measure the temperature of the junction of the light emitting diode by measuring a temperature of the interior of the case.

20. The light source of claim 15, wherein:

the light emitting diode comprises a representative light emitting diode and the light source includes a plurality of light emitting diodes:

the processor circuitry is further configured to supply the electrical current to the plurality of light emitting diodes based on the selected calibration factor identified from the measured temperature of the junction of the representative light emitting diode.

* * * * *